United States Patent [19]

Lee

[11] Patent Number: 5,072,730
[45] Date of Patent: Dec. 17, 1991

[54] KEY PROGRAMMED TRANSCUTANEOUS ELECTRIC STIMULATOR

[75] Inventor: John H. Lee, North Oaks, Minn.

[73] Assignee: Minnesota Mining and Manufacturing Company, St. Paul, Minn.

[21] Appl. No.: 538,154

[22] Filed: Jun. 14, 1990

[51] Int. Cl.⁵ .............................................. A61N 1/36
[52] U.S. Cl. .................................................. 128/421
[58] Field of Search ........ 128/419 P, 419 PG, 419 R, 128/421, 422; 200/43.06, 43.08

[56] References Cited

U.S. PATENT DOCUMENTS

| | | | |
|---|---|---|---|
| 2,376,846 | 5/1945 | Field et al. | 200/43.06 |
| 3,198,195 | 8/1965 | Chardack | 128/419 P |
| 3,738,369 | 6/1973 | Adams et al. | 128/419 PG |
| 4,198,552 | 4/1980 | Tahara | 200/43.06 |
| 4,365,633 | 12/1982 | Loughman et al. | 128/419 PG |
| 4,464,550 | 8/1984 | Soes | 200/43.06 |
| 4,642,769 | 2/1987 | Petrofsky | 128/421 |
| 4,926,864 | 5/1990 | Dufresne et al. | 128/421 |

Primary Examiner—William E. Kamm
Attorney, Agent, or Firm—Gary L. Griswold; Walter N. Kirn; John H. Hornickel

[57] ABSTRACT

A transcutaneous electrical stimulator for applying therapeutic electrical impulses to the living body of a patient, where at least some of the electrical parameters of the electrical impulses are actuated by the use of a key. When this key is inserted in the housing of the stimulator and rotated, the several wards actuate corresponding switches, activating a controller which operates a generator to deliver the therapeutic impulses. At least one parameter of the therapeutic impulses may be determined by the pattern of the wards.

10 Claims, 2 Drawing Sheets

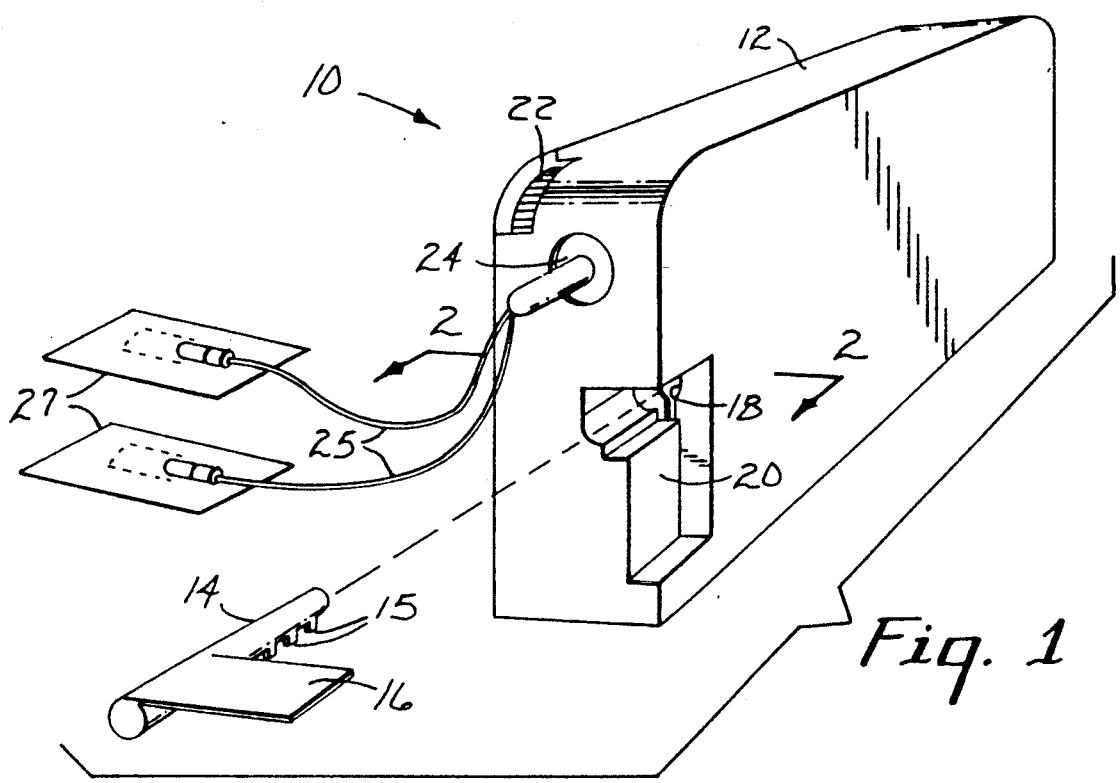
Fig. 1
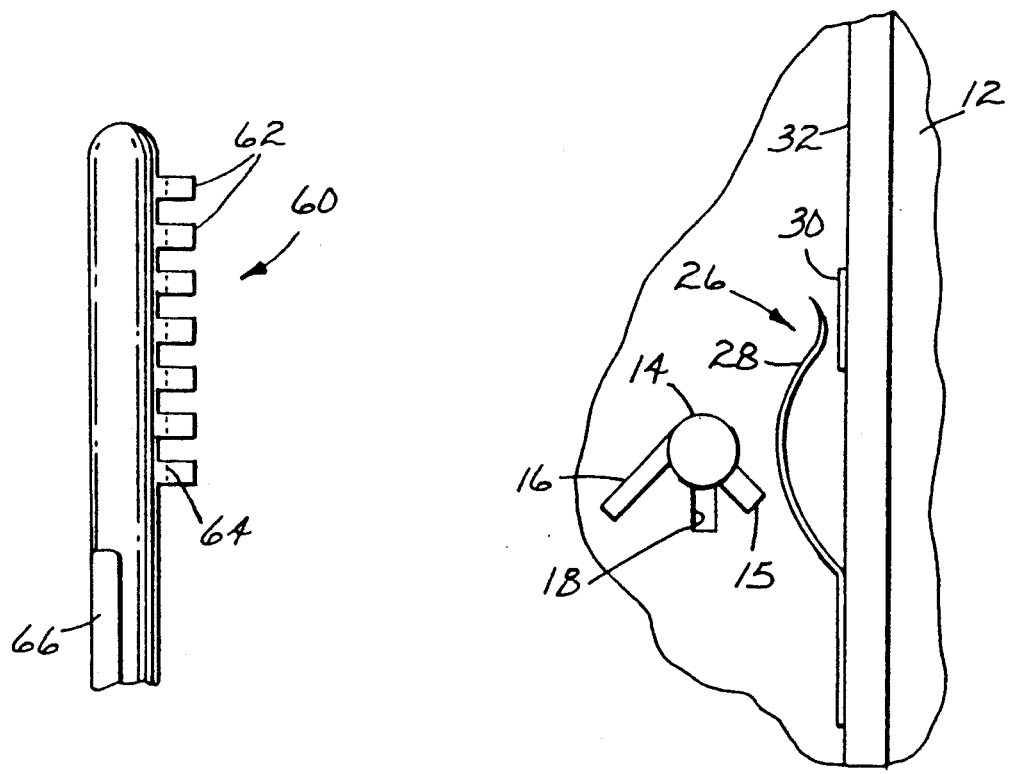
Fig. 4
Fig. 2

KEY PROGRAMMED TRANSCUTANEOUS ELECTRIC STIMULATOR

FIELD OF THE INVENTION

This invention relates to medical stimulators and the control of the electrical parameters used in the medical stimulators to deliver therapeutic electrical impulses.

BACKGROUND OF THE INVENTION

In recent years, transcutaneous electrical nerve stimulation (TENS) has been developed to provide relief of pain without the use of systemic analgesic drugs. Stimulators used for this purpose deliver therapeutic electrical impulses to the skin surface of a living patient through lead wires from the stimulator to body contacting electrodes. Typically, transcutaneous electrical stimulators control at least the therapeutic parameters of electrical pulse width, electrical pulse rate, and electrical pulse amplitude. Sometimes, the same stimulator may have dual controls for operating two separate transcutaneous electrical output channels.

Also in recent years, neuromuscular stimulation (NMS) has been developed to provide muscle re-education (maintenance, strengthening, or rehabilitation) transcutaneously.

Conventionally, the electrical pulse parameters have been controlled in the stimulator using either potentiometers or with momentary contact rocker switches. The latter are shown in coassigned U.S. Pat. No. 4,803,986 (Dufresne et al.), which is hereby incorporated by reference.

For purposes of describing this invention, a "transcutaneous electrical stimulator" includes at least a TENS stimulator, a NMS stimulator, or any other medical stimulator used to deliver therapeutic electrical impulses.

One difficulty with using conventional stimulators is dealing with the problem of setting the various electrical pulse controls for the proper and unique operation of the transcutaneous electrical stimulator for a patient because the stimulator is used therapeutically by untrained personnel. Sometimes, the stimulator is used by a patient apt to alter the controls in ignorance of the effect of such alteration.

The desired therapeutic effect of the electrical impulses can not occur if the controls are not properly set by trained personnel. Unfortunately, misapplication of the stimulator through improper setting of the controls can be painful to the patient at the very location requiring pain relief therapy.

Previously, the operation of electrical switches by a token using a plurality of multiple contact switches for use in dispatching systems has been disclosed in U.S. Pat. No. 3,046,364 (De Kramer et al).

Also, U.S. Pat. No. 4,647,734 (Dana) discloses a key activated switch providing binary coded switching outputs for use with microprocessor based equipment. An arrangement of actuators is also disclosed.

Also, U.S. Pat. No. 3,415,087 (Kramasz et al) discloses a plurality of electrical switches disposed in spaced relation to the cylinder of a pin tumbler lock. A special key is provided wherein one edge has conventional serrations for operating the pin tumbler, and the other edge has a plurality of lobes or notches formed into it which cooperate with a link mechanism that activates on or more of the electrical switches.

None of these prior activities has contemplated the circumstances unique to pain relief therapy using transcutaneous electrical stimulators.

SUMMARY OF THE INVENTION

The present invention solves the problems found in the operation of conventional transcutaneous electrical stimulators by providing a stimulator having a apertured housing which may receive an actuator such as a key having wards or other actuating means to control one or more of the electrical pulse parameters vital to the proper transcutaneous electrical therapy. Trained personnel having a variety of keys may select one key to provide the proper setting of the electrical pulse controls. The controls may not be reset by untrained personnel unless a different key is possessed.

The transcutaneous electrical stimulator comprises an apertured housing, means for generating therapeutic impulses of electrical energy, means for delivering the electrical energy to a location for therapy, and means for controlling the generating means, and a key insertable into the housing through the aperture and having a plurality of wards, at least one of which is configured to actuate the controlling means.

Typically, transcutaneous electrical stimulators control at least the parameters of electrical pulse width, electrical pulse rate, and electrical pulse amplitude.

Preferably, a stimulator of the present invention comprises a controller including several switches mounted within the housing but in communication with the aperture or keyhole. The operation of the stimulator involves a key to engage or otherwise actuate at least one of the switches. Preferably, the key has several wards, at least one of which is configured to engage at least one of the switches.

To use the stimulator, the key is inserted into the aperture and moved, e.g., rotated into a stationary position, so that the appropriate ward actuate the appropriate switches through direct contact or otherwise. Depending on the presence or length of each ward in communication with a corresponding switch, some of the switches are closed. The various combinations of ward-switch contacts sets the electrical pulse parameters desired for proper therapy. With the key maintained in a stationary position, the controller is activated so as to induce the therapeutic regimen of electrical stimulation from the generator selected by trained personnel for the patient.

The invention may also be embodied so that the electrical parameters of pulse rate and pulse width are determined by the pattern of the wards, while the electrical parameter of pulse amplitude is controlled by the patient using a potentiometer dial provided at the exterior surface of the stimulator housing.

Another embodiment of the invention provides that the key will be constructed with frangible wards which can be removed by hand or with a tool by the trained personnel. Selection of which wards to remove establishes the proper transcutaneous electrical therapy for the patient. By choosing which of the wards to remove, the practitioner can easily prepare a key which will invoke exactly the regimen of therapy believed to be most appropriate.

An object of the invention is to provide a mechanism so that the electrical parameters of the therapeutic impulses generated by a transcutaneous electrical stimulator can be quickly and simply set to pre-selected values without threat of misapplication of the transcutaneous electrical therapy through alteration of the values set.

A feature of the invention is a transcutaneous electrical stimulator having a keyhole and a matching key so that insertion and rotation of the key invokes these pre-selected values.

An advantage of the invention is that the stimulator with appropriate key may be provided to a patient without undue concern as to misuse of the transcutaneous electrical stimulator.

A further advantage of the invention is that the medical practitioner can specify a particular therapeutic mode by the selection of a particularly patterned key for a particular patient. When a key with a plurality of frangible wards is provided, that key is easily converted to a patterned key by breaking off the appropriate wards on the key.

A related advantage is that trained personnel providing a different key to a patient may alter the therapeutic regimen without other alteration to the transcutaneous electrical stimulator.

Yet another advantage of the invention is that the cost of providing transcutaneous electrical therapy can be reduced without loss of providing appropriate therapy for each patient.

BRIEF DESCRIPTION OF THE DRAWING

A more complete understanding of the invention and its advantages will be apparent from the Embodiments of the Invention taken in conjunction with the accompanying Drawing, in which:

FIG. 1 illustrates a perspective view of a transcutaneous electrical stimulator of the present invention with the key shown in dotted line relationship to the housing;

FIG. 2 illustrates a cross section view along section lines 2—2 in FIG. 1, emphasizing the interaction of the key with the switches;

FIG. 4 illustrates a key bearing frangible wards suitable for use with the present invention.

EMBODIMENTS OF THE INVENTION

Figure 3:
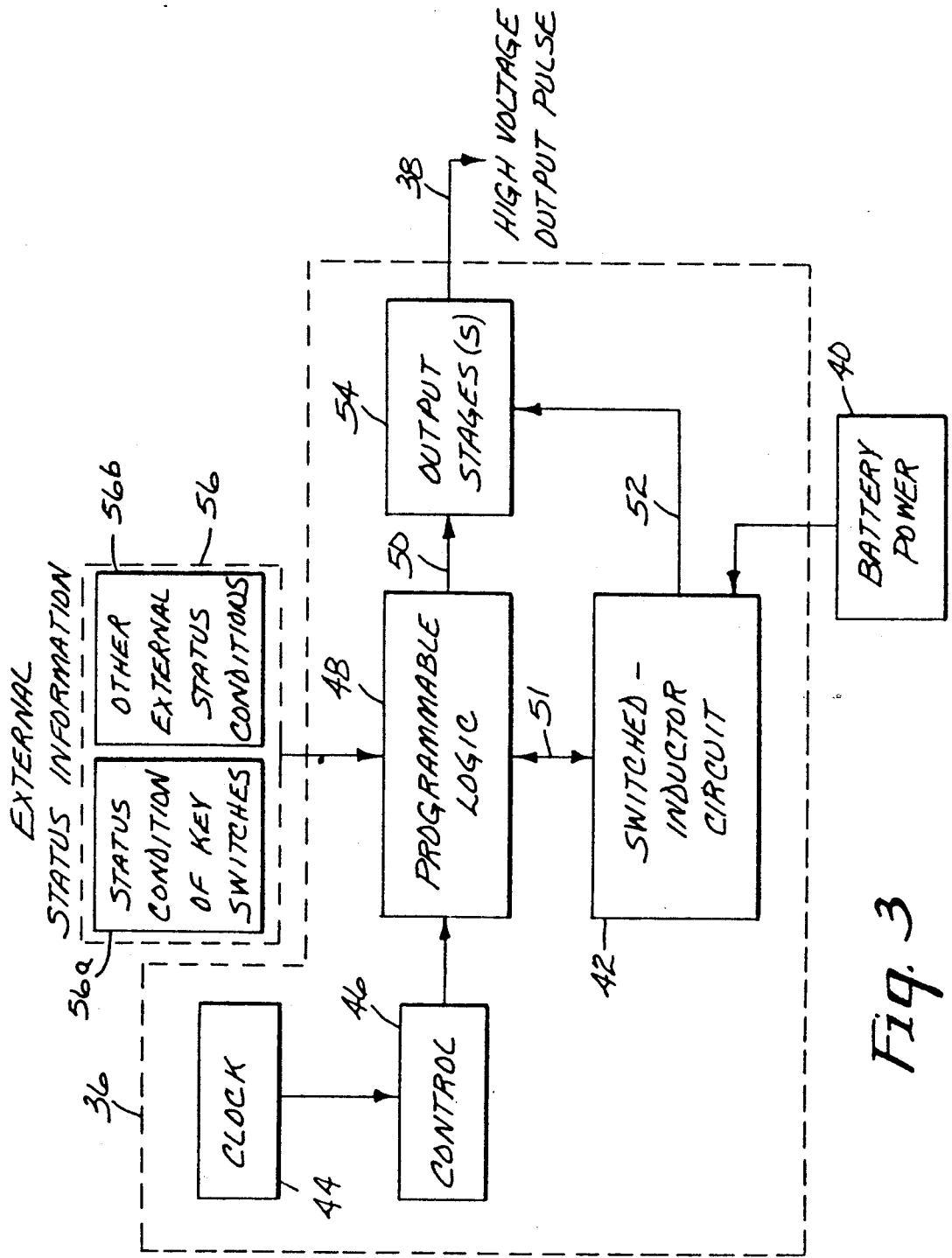
FIG. 3 illustrates a block diagram of the internal electrical components of the transcutaneous electrical stimulator of the present invention.

Referring to FIG. 1, a transcutaneous electrical stimulator of the present invention is shown. The stimulator 10 includes a housing 12 and a key 14. The key 14 bears at least one ward 15. The pattern of the wards 15 encodes information about the therapeutic regimen specified by that particular key used in the housing 12. The key 14 has a flange 16 at its head to facilitate grasping and turning.

The housing 12 has an aperture 18 adapted to receive the key 14. A support block 20 may be optionally provided to support and protect the key 14 when the key 14 is in its operating position. Optionally, the support block 20 may be configured to provide a detent mechanism (not shown) to resist movement of the key 12 in aperture once the key 12 is in its operating position.

Optionally mounted on the housing 12 is one or more potentiometer dials 22, used by the patient to adjust the pulse amplitude in certain embodiments of the invention.

Also mounted on the housing 12 is at least one output jack 24 which are used to convey the repetitive electrical pulses to the patient. Typically, a pair of lead wires 25 adapted to connect to output jack 24 conveys the repetitive electrical pulses to a pair of body contacting electrodes 27.

Referring to FIG. 2, a cross section view along section lines 2—2 in FIG. 1, the interaction of the key with the switches is illustrated. The housing 12 has been removed from the view for clarity, although it should be understood that the housing 12 would preferably include a structure, e.g., a keyway, aligned with the aperture 18, to support and align the key 14 when and while it is inserted in the housing 12. In this figure, the key 14 is being held supported but at liberty to rotate axially through an arc. At some point during rotation of the key 14, one or more wards 15 on the key 14 will actuate one or more switches 26, preferably by directly contacting the switches 26.

Each switch 26 may be formed from a spring contact 28 mounted on a printed circuit board 32 and a fixed contact 30, conveniently, an electrically conducting pad on a printed circuit board 32. Preferably, the wards 15 contact the spring contacts 28 which thereby contact fixed contacts 30.

Optionally, when at the point where rotation of the wards 15 contact the spring contacts 28, a detent mechanism on the support block 20 may releasably hold the key 14 in engagement with the switches 26.

Depending on the pattern of the wards 15 on the key 14, one or more of the switches 26 will be actuated. The arrangement of the switches actuated by the key determine the functioning of electrical circuitry in the stimulator 10 for providing pain relief therapy.

Referring to FIG. 3, a general block diagram of the electrical circuit 36 required to supply high voltage/-current output pulses 38 of the stimulator 10 is illustrated. Generally, battery power 40 is supplied to a switched inductor circuit 42. A clock 44 drives a control circuit 46, which in turn controls a programmable logic block 48. Programmable logic block 48 supplies switching signals 51 to switched inductor circuit 42 for generating a high-voltage supply 52 to output stages 54, which then utilizes programmed logic signal 50 to generate electrical stimulation signal 38. Programmable logic block 48 receives external status information 56 and uses this information to create the programmed logic signal 50 appropriate to the desired output conditions. Included in the external status information 56 is the condition of the switches 26 created by the pattern of contact between spring contact(s) 28 and fixed contact(s) 30 (these status conditions denoted collectively by the reference numeral 56a), and optionally, information on the condition of other controls and sensors (these status conditions denoted collectively by the reference numeral 56b) such as the potentiometer 22 (shown in FIG. 1.)

The block diagram of the electrical circuit 36 shown in FIG. 3 is illustrative of an electrical circuit of a transcutaneous electrical stimulator 10 of the present invention. It is to be recognized and understood that electrical circuits for use in transcutaneous electrical nerve stimulators are well known in the art and may include other circuitry or alterations to the circuitry shown here.

The particular electrical circuit 36 illustrated in FIG. 3 is preferred for use with the stimulator 10 of the present invention and is additionally described in coassigned U.S. Pat. application Ser. No. 042,166, filed Apr. 24, 1987, and now abandoned but continued in U.S. Pat. application Ser. No. 361,784, filed May 30, 1989, now U.S. Pat. No. 4,926,864, the contents of which are hereby incorporated by reference.

However, in an alternate embodiment of the invention, where low component count is particularly desired, the output stages can incorporate a transformer coupling, obviating the need for the switched inductor circuit 42 for the generation of high voltage. Exemplary output stages of this type are also well known to those skilled in the art.

Referring to FIG. 4, a key 60 bearing frangible wards 62 is illustrated. In this embodiment, the key 60 has been constructed so that the wards 62 are frangible at score lines 64. The score lines are formed on the wards 62 during the process of manufacturing the key 60. These score marks 64 are of such nature so that one or more wards 62 can be deliberately removed by hand or with a tool with some effort by the trained medical practitioner, in order to create the pattern of wards 62 on the key 60 desired to actuate the stimulator 10 to provide the appropriate pain relief therapy. However, the wards 62 should have sufficient mechanical strength at the score lines 64 to minimize inadvertent or accidental breaking. Other aspects of the key 60 are similar to key 14, such as the presence of a flange 66 corresponding to flange 16.

In preferred embodiments, the key 14 or 60 will be formed of a non-conductive material to prevent electrical conduction between the various switches 26 through the key. Polymeric materials are preferred, with polycarbonate considered particularly preferred. Such a key is advantageously made using injection molding techniques well known to those skilled in that art.

The spring contacts 28 of the preferred switches 26 are advantageously formed from hardened beryllium copper, optimally covered with a nickel or nickel/gold plating to improve conductivity. The fixed contacts 30 may be an electrically conductive pad of copper on the printed circuit board, optimally covered with gold plating to improve conductivity.

The remaining portions of the stimulator 10 may be made of materials conventionally used for transcutaneous electrical stimulators and the electrical circuitry therefor.

While certain embodiments of the present invention have been described in detail herein and as shown in the accompanying Drawing, it will be evident that various further modifications are possible without departing from the scope of the invention.

What is claimed is:

1. A transcutaneous electrical stimulator, comprising:
a key having one or more wards thereon;
a housing having an aperture therein, said housing further having a keyway aligned with said aperture, said aperture being adapted to admit said key and said keyway being adapted to support and align said key;
means enclosed within said housing for generating therapeutic electrical impulses of electrical energy, said generating means being adapted to respond to a pattern of status conditions and responsively modify the electrical parameters of the electrical impulses;
means for delivering the electrical energy to a location for therapy; and
means enclosed within said housing adjacent said keyway for controlling said generating means wherein said controlling means communicates to said generating means at least some of the status conditions to which said generating means is responsive; wherein
when said key is inserted into said keyway and rotated, said ward contacts and actuates said controlling means.

2. A transcutaneous electrical stimulator, according to claim 1, wherein said controlling means comprises a plurality of switches, each adapted to be contacted by a ward of said key when said key is rotated, and further adapted so that actuation of each switch is changed if contacted, and wherein the status conditions communicated to said generating means by said controlling means are determined by whether each switch is actuated or not actuated.

3. A transcutaneous electrical stimulator, according to claim 2, wherein said wards on said key are frangible, whereby said switches may be actuated by a pattern of wards unbroken from said key.

4. A transcutaneous electrical stimulator, according to claim 3, wherein said wards have score lines for frangibility.

5. A transcutaneous electrical stimulator, according to claim 2, wherein said wards on said key are non-conductive.

6. A transcutaneous electrical stimulator, according to claim 1, wherein the electrical parameters of the electrical impulses which are responsively modified by said generating means include the electrical parameters of pulse rate and pulse width.

7. A transcutaneous electrical stimulator, according to claim 6, wherein the status conditions communicated to said generating means by said controlling means includes said pulse rate and said pulse width.

8. A transcutaneous electrical stimulator, according to claim 7, wherein said controlling means comprises a plurality of switches, each adapted to be contacted by a ward of said key when said key is rotated, and further adapted so that actuation of each switch is changed if contacted, and wherein the status conditions communicated to said generating means by said controlling means are determined by whether each switch is actuated or not actuated and wherein at least one ward on said key actuates at least a corresponding switch, whereby said switches actuated by said wards determine said pulse rate and said pulse width.

9. A transcutaneous electrical stimulator, according to claim 1, further comprising a potentiometer, wherein the electrical parameters of the electrical impulses which are responsively modified by said generating means include the electrical parameter of pulse amplitude, and further wherein the status conditions which cause the pulse amplitude to be responsively modified depend of the setting of said potentiometer.

10. A transcutaneous electrical stimulator, according to claim 1, wherein said housing further comprises a means for releasably holding said key in said keyway.

* * * * *